( 12 ) United States Patent
Urushihara et al.

(10) Patent No.: US 7,244,452 B2
(45) Date of Patent: Jul. 17, 2007

(54) MEMBER EXCELLENT IN ANTIBACTERIAL ANTIMOLD AND/OR ANTIALGAE EFFECTS AND PROCESS FOR PRODUCING THE SAME

(75) Inventors: Wataru Urushihara, Kobe (JP); Takenori Nakayama, Kobe (JP); Sadako Yamada, Kobe (JP)

(73) Assignee: Kobe Steel, Ltd., Kobe-shi (KR)

( * ) Notice: Subject to any disclaimer, the term of this patent is extended or adjusted under 35 U.S.C. 154(b) by 711 days.

(21) Appl. No.: 10/466,547

(22) PCT Filed: Aug. 15, 2002

(86) PCT No.: PCT/JP02/08296

§ 371 (c)(1),
(2), (4) Date: Jul. 24, 2003

(87) PCT Pub. No.: WO03/016595

PCT Pub. Date: Feb. 27, 2003

(65) Prior Publication Data

US 2004/0047899 A1   Mar. 11, 2004

(30) Foreign Application Priority Data

Aug. 20, 2001   (JP)   ............................. 2001-250465
Apr. 20, 2002   (JP)   ............................. 2002-116678

(51) Int. Cl.
*A01N 59/16* (2006.01)
*A01N 55/02* (2006.01)
*B32B 15/00* (2006.01)
*C25D 3/56* (2006.01)
*C25D 3/12* (2006.01)

(52) U.S. Cl. ...................... 424/646; 424/617; 514/501; 428/680; 205/258; 205/271

(58) Field of Classification Search ................ 424/617, 424/646; 205/258, 271; 428/680; 514/501
See application file for complete search history.

(56) References Cited

U.S. PATENT DOCUMENTS 4,846,940 A  *  7/1989  Neuhauser et al.  ......... 205/109

FOREIGN PATENT DOCUMENTS

| JP | 02093006  A | * | 4/1990 |
| JP | 07163511  A | * | 6/1995 |
| JP | 11-343592   |   | 12/1999 |
| JP | 2000-198709 |   | 7/2000 |

OTHER PUBLICATIONS

Lewis RJ, Hawley's Condensed Chemical Dictionary, Thirteenth Edition, pp. 118 and 802 (1997).*
http://www.answers.com/topic/Vickers-Hardness-Scale.*

* cited by examiner

*Primary Examiner*—Johann Richter
*Assistant Examiner*—Nathan W. Schlientz
(74) *Attorney, Agent, or Firm*—Oblon, Spivak, McClelland, Maier & Neustadt, P.C.

(57) ABSTRACT

Disclosed is a member which is superior in anti-fungus property and anti-alga property, and is coated with a surface treatment coating comprising at least a layer having anti-fungus property and/or anti-alga property laminated between a topmost surface functional layer and a base, wherein the layer having anti-fungus property and/or anti-alga property comprises 80% or more of Ni, 0.1 to 10% of P, and 0.0001 to 1% of hydrogen, holes reaching the surface of the layer having anti-fungus property and/or anti-alga property are present in the topmost surface functional layer so as to penetrate the topmost surface functional layer, the opening area ratio thereof to the total area when the topmost surface functional layer is viewed in plan being from 0.001 to 10%, or the elution amount of Ni is from 0.1 to 50 $\mu g/cm^2$/week when the member is immersed in still water at 30° C.

14 Claims, 4 Drawing Sheets

FIG. 1A
FIG. 1B
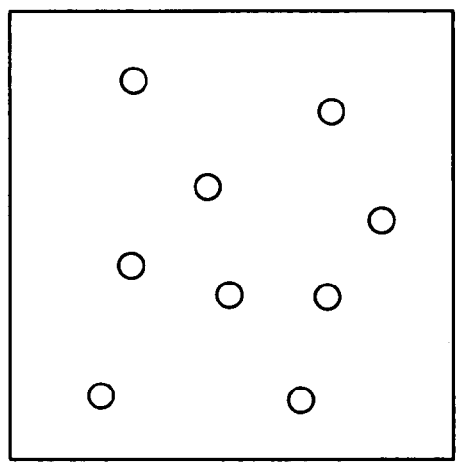
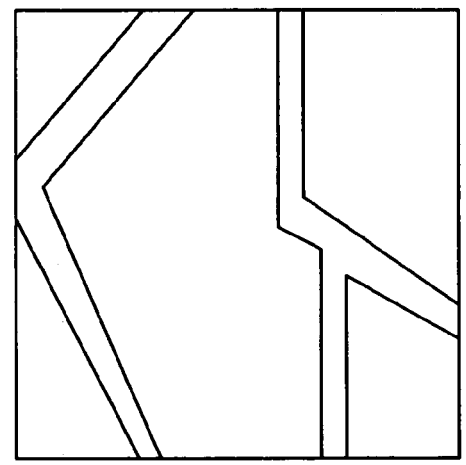
EXAMPLES OF HOLES IN THE TOPMOST SURFACE
FUNCTIONAL LAYER SURFACE O: HOLES WHICH PENETRATE THE TOPMOST SURFACE FUNCTIONAL LAYER TO REACH THE ANTI-FUNGUS LAYER
×: HOLE WHICH DOES NOT PENETRATE THE TOPMOST SURFACE FUNCTIONAL LAYER

US 7,244,452 B2

MEMBER EXCELLENT IN ANTIBACTERIAL ANTIMOLD AND/OR ANTIALGAE EFFECTS AND PROCESS FOR PRODUCING THE SAME

TECHNICAL FIELD

The present invention relates to a member capable of suppressing the propagation of at least one of bacteria, mold and algae, and a production process thereof.

BACKGROUND ART

In recent years, adoption of metal material to which antibacterial property, anti-mold property or anti-alga property is given has been investigated not only for applications in the food processing industry and the medical industry but also for diary necessities in order to block the growth of bacteria, mold, algae and so on from the viewpoint of hygiene.

The present inventors suggested metal materials caused to have antibacterial property, anti-mold property and anti-alga property (JP-A No. 11-343592 and JP-A No. 2000-198709). These metal materials (members) are made mainly of Ni, and are materials comprising, on the surface thereof, a coating in which P, Co, H and so on are controlled. The antibacterial property, anti-mold property, and anti-alga property thereof, and the persistence of these properties are better than those of conventional anti-fungus members.

However, in the above-mentioned members, the surface coating is caused to have such functions as antibacterial effect, anti-mold property effect and anti-alga effect; therefore, there may be cases in which other required properties (for example, hardness, discoloration resistance, fingerprint adhesion resistance, color tone, glossiness, corrosion resistance, scratch resistance, and so on) based on the structure of the surface cannot be sufficiently satisfied.

In light of the above-mentioned situations, the present invention has been made. An object thereof is to provide a member to which not only functions of suppressing the propagation of at least one of bacteria, mold or algae but also other functions based on the structure of its surface are given; and a production process thereof.

DISCLOSURE OF THE INVENTION

The anti-bacteria, anti-mold, and/or anti-alga member of the present invention, which can attain the above-mentioned object, has the following subject matter as a first embodiment: a member coated with a surface treatment coating comprising a layer having anti-bacteria, anti-mold, and/or anti-alga property present between an outermost surface functional layer and a base, wherein the thickness of the outermost functional layer is from 0.01 µm to 5 µm, holes reaching the surface of the layer having anti-bacteria, anti-mold, and/or anti-alga property are present in the outermost surface functional layer so as to penetrate the outermost surface functional layer, the opening area ratio thereof to the total area when the outermost surface functional layer is viewed in plan being from 0.001 to 10%, the elution amount of components of the outermost surface functional layer is 1 µg/cm$^2$/week or less when the member is immersed in still water at 30° C., and the layer having anti-bacteria, anti-mold, and/or anti-alga property comprises 80% (% means % by mass if it is not specified otherwise) or more of Ni, 0.1 to 10% of P, and 0.0001 to 1% of hydrogen.

A second embodiment of the present invention has the following subject matter: a member coated with a surface treatment coating comprising a layer having anti-bacteria, anti-mold, and/or anti-alga property present between an outermost surface functional layer and a base, wherein holes reaching the surface of the layer having anti-bacteria, anti-mold, and/or anti-alga property are present in the outermost surface functional layer so as to penetrate the outermost surface functional layer, the thickness of the outermost surface functional layer is from 0.01 µm to 5 µm, the elution amount of components of the outermost surface functional layer is 1 µg/cm$^2$/week or less when the member is immersed in still water at 30° C., the layer having a anti-bacteria, anti-mold, and/or anti-alga property comprises 80% or more of Ni, 0.1 to 10% of P, and 0.0001 to 1% of hydrogen, and the elution amount of Ni is from 0.1 to 50 µg/cm$^2$/week when the member is immersed in still water at 30° C.

In the member of the present invention, the layer having anti-bacteria. anti-mold, and/or anti-alga property has a function of suppressing the propagation of at least one of bacteria, mold or algae in both of the first and second embodiments. In the case that a member has at least one of the antibacterial effect, the anti-mold effect and the anti-alga effect, the wording "has at least one of the antibacterial effect, the anti-mold effect and the anti-alga effect" may be referred to as "has the effect of suppressing microorganism-propagation".

Metals contained in the outermost surface functional layer are preferably nobler than Ni in order to ensure superior antibacterial property, anti-mold property, and anti-alga property.

The member of the present invention preferably has a surface hardness Hv of 500 or more.

In order to heighten, for example, the discoloration resistance of the member of the present invention, it is recommendable that the outermost surface functional layer is a discoloration-resistant functional layer made mainly of at least one selected from the group consisting of Cr, alloy containing 80% or more of Cr, Cr oxide, Cr carbide, Cr nitride, and complex oxide containing Cr.

The member of the present invention wherein the discoloration resistance thereof is heightened in this way is suitable, for example, for water-associated articles.

The present invention embraces a process for producing the above-mentioned member, comprising the step of forming an intermediate layer comprising a layer having anti-bacteria, anti-mold, and/or anti-alga property and an outermost surface functional layer on a base, and subsequently subjecting the resultant to electrolysis treatment or immersion treatment in an acidic solution having a pH of 7 or less in such a manner that the amount of Ni eluting into the acidic solution is from 0.1 to 100 µg/cm$^2$. In particular, in the case that the outermost surface functional layer is formed by wet plating treatment, a preferred embodiment is a process in which the electrolysis treatment is subsequently conducted in the plating bath.

In the present specification, the "layer having anti-bacteria, anti-mold, and/or anti-alga property" is represented by the "anti-fungus layer" hereinafter.

BRIEF DESCRIPTION OF THE DRAWINGS

FIGS. 1 are explanatory views of holes present in the surface of an outermost surface functional layer according to the member of the present invention.

BEST MODES FOR CARRYING OUT THE INVENTION

Figure 2:
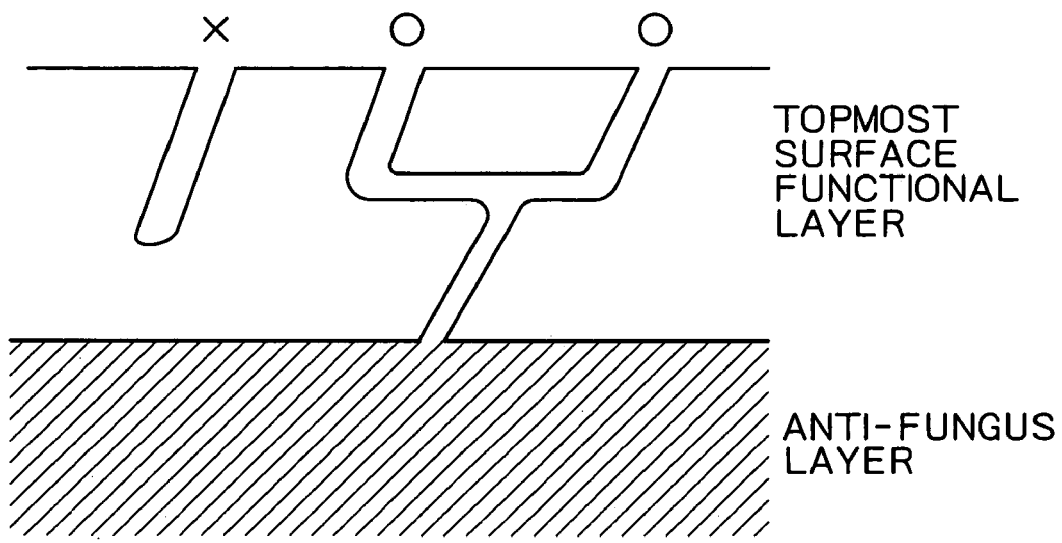
FIG. 2 is an explanatory view of a hole penetrating the outermost surface functional layer to reach the surface of an anti-fungus layer.

The member of the present invention has a maximum characteristic by disposing a surface treatment coating having the above-mentioned anti-fungus layer which can give at least one of antibacterial property, anti-mold property, and anti-alga property and further having an outermost surface functional layer which gives other functions required for the member and does not block the effect of the anti-fungus layer.

Examples of the base used in the member of the present invention include nonferrous metals or alloys such as aluminum, titanium and brass, iron-based alloys such as stainless steel, and composite metal materials thereof.

The surface treatment coating according to the member of the present invention has a structure wherein an anti-fungus layer is present (that is, at least an anti-fungus layer is laminated) between an outermost surface functional layer and the base. The outermost surface functional layer, out of these, is a layer for ensuring other functions than the antibacterial property, anti-mold property and anti-alga property which are required for the member of the present invention. The anti-fungus layer is a layer for ensuring at least one of the antibacterial property, anti-mold property and anti-alga property. The anti-fungus layer is preferably a layer having all of the antibacterial property, anti-mold property and anti-alga property.

It is considered that the effect of suppressing microorganism-propagation in the member of the present invention is attained by the following matter: ions of components of the anti-fungus layer elute into adsorption water present on the surface of the surface treatment coating, the amount of the water being usually from about 10 nm to 1 μm and being from several tens to several hundreds micrometers in high-humidity atmosphere, and then these ions contact and die bacteria and so forth which appear to propagate through the adsorption water. However, in the structure wherein the outermost surface functional layer is disposed as the outermost surface of the surface treatment coating, the anti-fungus layer is not naked; therefore, the ions of the anti-fungus layer components cannot elute onto the surface of the surface treatment coating, as described above.

Thus, in the member of the present invention, adopted is a structure wherein holes reaching the surface of the anti-fungus layer are made in the outermost surface functional layer to penetrate the outermost surface functional layer, (which holes may be referred to merely as the "through holes" hereinafter). The "holes" referred to in the present invention include (a) circular opened holes present in the outermost surface functional layer, and further (b) linear opened holes, or opened holes having a complicated shape, as illustrated in FIGS. 1. The through holes easily hold the above-mentioned adsorption water, and further the anti-fungus layer component ions which elute out through the through holes diffuse satisfactorily onto the surface of the surface treatment coating by capillarity caused in the through holes. Thus, it has been found out that even if the through holes are made in such a degree that the functions of the outermost surface functional layer are not damaged, sufficient effect of suppressing microorganism-propagation can be ensured. As a result, the present invention has been completed.

The member of the present invention needs to satisfy either of the requirements of the first embodiment or the requirements of the second embodiment.

In the first embodiment of the present invention, about the through holes which reach the surface of the anti-fungus layer and are present in the outermost surface functional layer, the opening area ratio thereof to the total area when the outermost surface functional layer is viewed in plan is set to 0.001% or more and 10% or less. In other words, the ratio of the area which is not covered with the outermost surface functional layer so as to be naked to the surface opposite to the base of the anti-fungus layer (the ratio being referred to as the "naked area ratio" hereinafter) is 0.001% or more and 10% or less. In the case that the through holes are present at a ratio within the above-mentioned range to the area of the outermost surface functional layer (that is, in the case that the naked area ratio of the anti-fungus layer is within the above-mentioned range), the effect of suppressing the propagation of microorganisms can be sufficiently ensured without damaging the function of the outermost surface functional layer.

That is, if the area ratio of the through holes is less than the above-mentioned range (that is, if the naked area ratio of the anti-fungus layer is less than the above-mentioned range), the effect of suppressing microorganism-propagation cannot be sufficiently ensured. It appears that this is because the elution amount of ions of the anti-fungus layer components becomes small. Preferably, the ratio is 0.01% or more by area. On the other hand, if the area ratio of the through holes is more than the above-mentioned range (that is, the naked area ratio of the anti-fungus layer is more than the above-mentioned range), the effect of holding the adsorption water or the effect of capillarity gets small so that the effect of suppressing microorganism-propagation trends to be conversely lowered. Moreover, the function of the outermost surface functional layer is damaged. Preferably, the ratio is 1% or less by area.

The area ratio of the through holes (the naked area ratio of the anti-fungus layer) in the member of the present invention [the following S2 (%)] is a value obtained as follows.

[1] Five fields of the surface of the outermost surface functional layer are observed with a scanning electron microscope or a transmission electron microscope (both of the microscopes being referred to as an "electron microscope"), the fields being dependently on the size of holes (examples of the fields include 1 μm×1 μm, 10 μm×10 μm, 100 μm×100 μm, 1 mm×1 mm, and 10 mm×10 mm). The area ratio S1 (%) of the holes in the outermost surface functional layer surface (the opening area ratio of the holes to the total area when the outermost surface functional layer is viewed in plan) is measured with an image processing device.

[2] A vertical section of the member of the present invention from the outermost surface of the surface treatment coating to the rear face of the base is observed with the electron microscope. The ratio X (%) of the number of the through holes reaching the surface of the anti-fungus layer to the holes present in the outermost surface functional layer surface, the number of the holes being 20 or more, is calculated for each member. For example, as illustrated in FIG. 2, in the case that two holes in the outermost surface functional layer surface are bonded to each other in the layer to penetrate the surface to reach the anti-fungus layer surface, the ratio X of the holes is calculated with the number of these through holes being 2. Thus, in the case of FIG. 2, the number of the holes present in the outermost surface functional layer surface is 3, and the number of the through holes to reach the anti-fungus layer surface, out of these holes, is 2. Therefore, X=66.6%.

[3] From the above-mentioned area ratio S1 (%) and the -ratio X (%) of the number of the through holes reaching the anti-fungus layer surface to the number of the holes present in the outermost surface functional layer surface, the area ratio S2 (%) of the through holes is calculated, using the following equation (1):

$$S2=S1 \times X/100 \quad (1)$$

The diameter of the holes present in the outermost surface functional layer surface, example of which include the above-mentioned through holes, is not limited. The average value obtained with the image processing device is desirably 0.1 μm or more and 1000 μm or less, more preferably 0.1 μm or more and 100 μm or less in the observed fields in the method

[2] of measuring the area ratio of the through holes. Since such a hole diameter makes it possible to produce the above-mentioned adsorption water holding effect and capillarity effect, good effect of suppressing microorganism-propagation can be ensured and further the function of the outermost surface functional layer cannot be damaged.

In the second embodiment of the member of the present invention, the elution amount of Ni is set to 0.1 μg/cm²/week or more and 50 μg/cm²/week or less when the member is immersed in still water at 30° C. Ni is a component which mainly constitutes the anti-fungus layer. As will be described later, Ni is combined with P and hydrogen to exhibit the effect of suppressing microorganism-propagation synergistically. Thus, in the case that the Ni elution amount is less than the above-mentioned range under the above-mentioned conditions, the amount of Ni elusion to the surface of the member is small in an ordinary use state. Thus, the effect of suppressing microorganism-propagation becomes insufficient. Preferably, the amount is 1 μg/cm²/week or more.

On the other hand, when the Ni elusion amount is more than the above-mentioned range, the function of the outermost surface functional layer may be damaged. Furthermore, for example, in the case that the member of the present invention is used in an ornament or the like, the member may cause metal allergy. Preferably, the amount is 20 μg/cm²/week or less. Usually, such a Ni elution amount can be ensured by causing the above-mentioned through holes to be present in the outermost surface functional layer at an area ratio within the above-mentioned range.

The Ni elution amount is a value obtained by putting 50 mL of ion exchange water into a 500-mL beaker, setting the temperature of the water to 30° C., immersing in this water the whole of a member sample having an outermost surface functional layer area of 25 cm² for one week, and then measuring the amount of Ni in the ion exchange water by ICP emission spectral analysis.

The following will describe structures common to the first embodiment and the second embodiment of the member of the present invention.

The thickness of the outermost surface functional layer is 0.01 μm or more and 5 μm or less. If the thickness of the outermost surface functional layer is less than the above-mentioned range, the function to be given by the outermost surface functional layer may not be sufficiently exhibited and the outermost surface functional layer is not easily formed to have an even thickness. Preferably, the thickness is 0.05 μm or more.

On the other hand, if the thickness of the outermost surface functional layer is more than the above-mentioned range, the effect of suppressing microorganism-propagation is lowered. It appears that this is because the distance along which the eluting ions of the anti-fungus layer components diffuse through the adsorption water to the outermost surface functional layer surface becomes long so that the amount of the ions which can reach the outermost surface functional layer surface falls. Preferably, the thickness is 0.5 μm or less.

The thickness of the outermost surface functional layer can be obtained by averaging the thicknesses measured in the respective fields obtained in the [2] of the method of measuring the area ratio of the through holes.

In the case that the thickness of the outermost surface functional layer or the presence of the through holes is not easily observed, for example, in the case that the thickness of the outermost surface functional layer is small so as to be less than the range of the present invention, the area ratio of the through holes or the thickness of the outermost surface functional layer can be measured by subjecting the layer to copper-plating with a copper sulfate bath or electroless Ni—P plating, and subsequently performing the above-mentioned method of measuring the through holes, area ratio. In the case that the thickness of the outermost surface functional layer is too small to be easily observed by such a method, the thickness of the outermost surface functional layer can be obtained by measuring a change in the mass of the member sample or analyzing a solution obtained by dissolving the outermost surface functional layer into a solvent by ICP emission spectral analysis. Furthermore, dependently on the material of the outermost surface functional layer, the through hole area ratio S2 (%) can also be obtained by measuring the current value A when a film made only of the anti-fungus layer components is at a natural electrode potential or is polarized into a certain potential, a current value B when a film made only of the outermost surface functional layer components is at a natural electrode potential or is polarized into a certain potential, and a current value C when the outermost surface functional layer surface of the member is at a natural electrode potential or is polarized into a certain potential, and using the following equation. In the following equation, "|B-C|" and "|A-B|" means the absolute values of the "|B-C|" and "|A-B|", respectively.

$$S2=100 \times (|B-C|)/(|A-B|)$$

It has already been confirmed that the area ratio of the through holes or the thickness of the outermost surface functional layer which can be obtained by these alternative methods are substantially equal to values obtained by the above-mentioned method of measuring the through holes area ratio. Thus, the values obtained by these alternative methods can be sufficiently adopted. However, in the case that the thickness of the outermost surface functional layer is within the above-mentioned given range, it can be usually measured by the above-mentioned method of measuring the through holes area ratio, which method is performed with an electron microscope without any copper plating.

The elution amount of the components of the outermost surface functional layer is 1 µg/cm²/week or less when the member of the present invention is immersed in still water at 30° C. If the elution amount of the outermost surface functional layer components is more than the above-mentioned range, the outermost surface functional layer is early consumed. Thus, the function given by the outermost surface functional layer is not kept over a long time. The elution amount is preferably 0.1 µg/cm²/week or less. As the elution amount of the outermost surface functional layer is smaller, the member is more preferred. Thus, the elution amount is most preferably 0 µg/cm²/week.

The elution amount of the outermost surface functional layer components can be measured by putting 50 mL of ion exchange water into a 500-mL beaker, setting the temperature of the water to 30° C., immersing in this water the whole of a member sample having an outermost surface functional layer area of 25 cm² for one week, and then measuring the amount of the outermost surface functional layer components in the ion exchange water.

The anti-fungus layer according to the member of the present invention comprises: Ni: 80% or more, P: 1-10%, and hydrogen: 0.0001-1%.

Ni does not have anti-mold property or anti-alga property originally, but has antibacterial property in some degree. It is presumed that P reacts with hydrogen to form a hydride having antibacterial effect and anti-mold effect and elute out. Since hydrogen has reducing effect, it is presumed that the reducing hydride is effective, in particular, for denaturation of proteins; therefore, it appears that hydrogen has an effect of killing bacteria, mold and algae.

Additionally, by the reducing effect of hydrogen, the outermost surface functional layer surface is prevented from being oxidized and the surface is activated; therefore, the formation of passivity coatings on the surface is suppressed. Thus, Ni or P can be continuously eluted out and the antibacterial property, anti-mold property and anti-alga property are kept over a long time.

By causing the anti-fungus layer to comprise effective components such as Ni, P and hydrogen in this way, good antibacterial property, anti-mold property and anti-alga property can be continuously kept. Furthermore, in any anti-fungus layer containing only a single effective component, the propagation of bacteria having resistance against the effective component cannot be suppressed. However, in the anti-fungus layer according to the present invention, the effects of the plural effective components also make it possible to prevent the propagation of bacterial resistant against specific one of effective components. It can be considered that it is very effective to combine, in particular, different effects of suppressing microorganism-propagation, such as the heavy metal effect which Ni has and the protein denaturation effect which the reducing hydride has.

In the member of the present-invention, the naked area ratio of the anti-fungus layer, that is, the elution area of the anti-fungus layer component ions is made small by disposing the outermost surface functional layer. It is therefore necessary to make the content of the effective components higher than in conventional anti-fungus members.

The Ni content in the anti-fungus layer according to the present invention is 80% or more. If the Ni content is less than 80%, the effect of suppressing microorganism-propagation becomes insufficient. It appears that this is because the Ni ion elution amount for ensuring the effect of suppressing microorganism-propagation sufficiently cannot be obtained. The Ni content is preferably 90% or more.

The P content in the anti-fungus layer according to the present invention is 0.1% or more and 10% or less. If the P content is less than the above-mentioned range, sufficient effect of suppressing microorganism-propagation cannot be ensured. The P content is preferably 1% or more. On the other hand, if the P content is more than the above-mentioned range, the effect of suppressing microorganism-propagation is conversely lowered. The P content is preferably 3.5% or less.

The hydrogen content in the anti-fungus layer is 0.0001% or more, and 1% or less. If the hydrogen content is less than the above-mentioned range, sufficient effect of suppressing microorganism-propagation cannot be ensured. The hydrogen content is preferably 0.001% or more. On the other hand, if the hydrogen content is more than the above-mentioned range, the toughness of the surface treatment coating is remarkably lowered so that the coating may be cracked and the function of the surface treatment coating (the function of the outermost surface functional layer and the function of the anti-fungus layer) may be damaged.

The hydrogen content is the amount of hydrogen released when the temperature of the coating layer which is mechanically peeled from the base is raised from room temperature to 350° C., and is more specifically the value measured by heating the coating layer continuously up to 350° C. at a temperature-raising speed of 12° C./min., and then measuring the amount of generated hydrogen with an atmospheric pressure ionization mass spectrometer (API-MS).

The Ni-based coating which can be applied to the above-mentioned anti-fungus layer may be any coating which contains other various elements if the contents of Ni, P and hydrogen satisfy the above-mentioned ranges. Examples thereof include Ni—P based coatings made of Ni—P, Ni—Co—P, Ni—P—B, Ni—Co—P—B, Zn—Ni—P or Fe—Ni—P and having a hydrogen-adsorbing amount adjusted into the range of 0.0001 to 1%; and composite coatings wherein the following are dispersed in these coatings: hard particles (such as SiC, $Si_3N_4$, $SiO_2$, TiC, TiN, WC, $Al_2O_3$, $ZrO_2$, $Cr_3C_2$, $Cr_2O_3$ and diamond particles); self-lubricating particles (such as polytetrafluoroethylene, fluorinated graphite, $WS_2$, $CaF_2$, BN, $MoS_2$ and graphite); photocatalyst functional particles (such as $TiO_2$, ZnO, $Nb_2O_5$, $SnO_2$, $ZrO_2$, CdS, ZnS, and $SrTiO_2$); and so on.

The thickness of the anti-fungus layer is not particularly limited. Considering the persistence of the effect of suppressing microorganism-propagation and economy, it is advisable to set the thickness to about 0.1 µm to 100 µm, more generally about 1 µm to 20 µm.

The surface treatment coating according to the present invention may be a laminate wherein two layers of an outermost surface functional layer and an anti-fungus layer are laminated onto each other, or may be made into a laminate structure having three or more layers by arranging a different layer between the outermost surface functional layer and the anti-fungus layer or between the anti-fungus layer and the base in order to make the adhesiveness, leveling property and so on high.

Needles to say, in the case that the different layer is arranged between the outermost surface functional layer and the anti-fungus layer, the through holes penetrating the outermost surface functional layer to reach the surface of the anti-fungus layer must also be present in this layer. In this case, the thickness of the outermost surface functional layer is a thickness from the anti-fungus layer surface to the outermost surface of the outermost surface functional layer (surface treatment coating surface), including the thickness of the different layer. This is because even if the thickness of only the outermost surface functional layer satisfies the above-mentioned range, the ions of the anti-fungus layer components diffuse insufficiently onto the surface of the surface treatment coating surface if the distance from the anti-fungus layer surface to the outermost surface of the outermost surface functional layer is made long by the formation of the different layer.

The above-mentioned outermost surface functional layer is a layer giving functions other than anti-fungus property to the member of the present invention, as described above. The material making the outermost surface functional layer is not particularly limited, and is appropriately selected dependently on functions required for the member.

Examples of the functions which are required for the member of the present invention and given by the outermost surface functional layer include hardness, discoloration resistance, fingerprint adhesion resistance, color tone, glossiness, corrosion resistance, and scratch resistance. Such functions are used so that the member of the present invention can be used for water-associated articles, which will be described later; machines for producing food or drinks; transporting, filling and packaging machines; and various building materials or decorating materials used in food, medical, welfare and other fields.

However, in the case that the metal contained in the outermost surface functional layer is baser than Ni, the ionization of Ni, which is a main component of the anti-fungus layer, is blocked and the effect of suppressing microorganism-propagation is lowered. Additionally, the elution amount of the outermost surface functional layer increases and the persistence of the functions given by the outermost surface functional layer is also lowered. Thus, the metal contained in the outermost surface functional layer is preferably nobler than Ni. It is determined on the basis of a natural electrode potential in water at 30° C. whether a metal is baser or nobler than Ni. In the case that the different layer is arranged between the outermost surface functional layer and the anti-fungus layer, any metal contained in this different layer is preferably nobler than Ni.

Considering the scratch resistance, the impact resistance and so on of the outermost surface functional layer when the member of the present invention is subjected to impact or abrasion, it is recommended that the surface hardness Hv is 500 or more, preferably 800 or more.

Articles to which the member of the present invention can be applied are various articles, examples of which include not only articles which need the effect of suppressing microorganism-propagation slightly in order to supply a good impression of high hygiene but also articles wherein importance is attached to the immediate affectivity or persistence of the effect of suppressing microorganism-propagation. Articles as follows correspond to the latter: instruments used in hospitals or medical facilities; equipment, building materials, lavatories, sanitary articles, air-conditioners, washing machines, refrigerators, carriers, and trucks used in food-manufacturing facilities or the food-service industry; waterways for cooling water in power stations or various factories; ships and ship parts; underwater structures and ocean facilities; and so on. Members having superior, immediately-effective and persistent effect of suppressing microorganism-propagation are required for the latter. Furthermore, the matter that discoloration is not generated, that is, discoloration resistance in addition to these properties is required in articles used in association with water, such as food-manufacturing facilities or kitchen equipment, sanitary parts such as lavatories, washstands, and water supply pipes, washing machines, drying machines, water channels for cooling water, ships, ship parts, underwater structures, ocean facilities and so on.

However, when the surface treatment coating is made only of the above-mentioned anti-fungus layer, the surface of the member may get discolored dependently on use environment. Thus, in the case that the member of the present invention is used in such articles, the member preferably has discoloration resistance. This may be attained by using a material having discoloration resistance in the topmost surface functional layer.

Specifically, it is preferred to adopt a material which is mainly made of at least one selected from Cr, alloy containing 80% or more of Cr, Cr oxide, Cr carbide, Cr nitride, and complex oxides containing Cr. The coatings obtained by these materials can easily be treated and have high discoloration resistance. The wording "is mainly made of an element" means that the element occupies 80% or more by mass of 100% by mass of all components of the topmost surface functional layer.

Specific examples of such a topmost surface functional layer include plating coatings made of Cr, Cr—C, Cr—Ni and the like; chemically treated coatings made of chromium oxide, chromium phosphate, chromium hydroxide and the like; coatings (reaction-type dry plating coatings according to arc ion plating or the like) made of CrN, CrCN, CrTiN and the like; and sodium chromate, ammonium chromate, zinc chromate, lead chromate and the like.

The member of the present invention wherein a chromium-based compound as described above is adopted as the material of the topmost surface functional layer is particularly suitable for water-associated articles used in food-manufacturing facilities, kitchen equipment, sanitary parts such as lavatories, washstands and water supply pipes, washing machines, drying machines, water channels for cooling water, ships, ship parts, underwater structures, ocean facilities and so on.

Besides, examples of the material of the topmost surface functional layer which can be adopted for the member of the present invention include various metals and alloys such as Sn, Pt, Au, Ni and Sn—Ni, various inorganic compounds such as oxides, nitrides and carbides thereof, and organic compounds such as organic resins.

The member of the present invention is produced by forming the surface treatment coating on a surface of the base exemplified above. Various methods such as electric plating, electroless plating, gas-phase plating, coating, and compression bonding can be adopted as the method for forming the Ni-based coating, which is the anti-fungus layer, and the method is not particularly limited. A simpler method is electric plating.

The method for increasing the hydrogen-adsorbing amount of the anti-fungus layer is not particularly limited. Ordinary examples thereof include a method of forming the coating and then exposing the coating to high-temperature hydrogen gas atmosphere, and a method of subjecting the layer to electrochemical hydrogen-charging. In the case that electric plating is adopted, hydrogen reaction, which is one of cathode reactions, is used to control electric current efficiency, whereby the hydrogen-adsorbing amount can easily be increased.

As the formation of the topmost surface functional layer, the following can be adopted: for example, wet plating characterized by a porous body, such as Cr plating; porous plating which can be formed very initially by ordinary wet plating or dry plating such as vapor deposition or arc ion plating (AIP); chemical treatment such as chromate treatment, phosphate treatment or water glass treatment; oxidization treatment; the formation of a porous inorganic coating made of concrete or the like; porous coating; or use of a porous state which is formed at a very initial stage of ordinary coating.

Besides, the above-mentioned through holes can be made by adopting a method of forming the topmost surface functional layer and subsequently applying stress to the member to generate cracks; a method of growing crystal of the material making the topmost surface functional layer abnormally in one direction (direction perpendicular to the coating layer surface); a method of incorporating a material which can be dissolved in a solvent to form the topmost surface functional layer, and subsequently removing this material with a solvent; or the like.

Specifically, for example, about organic resin, it is necessary to make the solid content in a bath for electrodeposition coating as small as about 1 to 10% and control the electrodeposition time to several seconds to about 30 seconds, thereby making the organic resin evenly thin.

About plating, it is necessary to use known treatment conditions to control the treating time to a very short time (several seconds to about 30 seconds).

When the topmost surface functional layer of the member of the present invention is formed, there may be caused a case in which Ni in the anti-fungus surface reacts to form a thin coating. Even if through holes penetrating the topmost surface functional layer to reach the anti-fungus layer are attempted to be made in this case, this attempt is hindered by the above-mentioned Ni reaction coating so that the resultants cannot become true through holes. As a result, the elution amount of the ions of the anti-fungus layer components gets little; therefore, a sufficient effect of suppressing microorganism-propagation may not be ensured. In many cases, the above-mentioned Ni reaction coating is formed, in particular, when the layer is formed by the wet plating treatment, chemical treatment, oxidization treatment or the like, which is exemplified above. The formation of the Ni reaction coating is affected by treatment solution such as plating solution or chemical treating solution.

The inventors repeatedly investigated to avoid a drop in the effect of suppressing microorganism-propagation based on the presence of the Ni reaction coating. As a result, it has been found out that by forming the anti-fungus layer and the topmost surface functional layer and subsequently immersing the resultant into a specified solution or subjecting the resultant to electrolysis treatment, the Ni reaction coating is activated and Ni in the coating elutes out so that the coating present in the through hole portions can be removed. In this way, holes extending from the topmost surface functional layer to the anti-fungus layer surface become through holes so that the elution amount of the anti-fungus layer component ions which is required for suppression of microorganism-propagation can be ensured.

The treatment solution used in the electrolysis treatment or immersion treatment is an acidic liquid having a pH of 7 or less. The use of this treatment solution makes it possible to elute Ni in the Ni reaction coating and remove the coating. In the case that the above-mentioned treatment is conducted in a liquid having a pH of more than 7, Ni falls into a passive state and the Ni reaction coating cannot be removed and further the Ni reaction coating may be conversely inactivated. The pH of the treatment solution is more preferably 3 or less, still more preferably 1 or less. As the pH is lower, the effect of removing the Ni reaction coating gets larger. Specific examples of the treatment solution include hydrochloric acid, sulfuric acid, nitric acid, chromic acid, phosphoric acid, acetic acid, acidic plating solution and oxidizer solution. These are used alone or a mixture wherein two or more thereof are appropriately mixed can be used.

The concentration and the temperature of the above-mentioned treatment solution, or the current density, the treatment time and so on at the time of electrolysis treatment are decided in accordance with the amount of Ni eluting into the treatment solution in the immersion treatment or electrolysis treatment. For example, as the concentration of the treatment solution is higher, the temperature thereof is higher and the current density in the electrolysis treatment is larger, the time for the treatment can be made shorter. The electrolysis treatment is more preferred than the immersing treatment since the treatment time can be made shorter even if the treatment solution having a low concentration is used.

As the method for the electrolysis, there can be used electrolysis giving a time when the member becomes an anode, such as anode constant-current electrolysis, anode constant-voltage electrolysis, alternating current electrolysis, or pulse electrolysis (electrolysis wherein electric current is reversed at regular time intervals). In the case that the formation of the topmost surface functional layer is conducted by wet plating treatment, the topmost surface functional layer is formed and subsequently electrolysis treatment can be conducted in the plating bath. Thus, this method is preferred since the Ni reaction coating can be more easily removed.

The immersion treatment or electrolysis treatment is conducted until the Ni amount which elutes in the treatment solution is 0.1 μg/cm$^2$ or more and 100 μg/cm$^2$ or less, preferably 1 μg/cm$^2$ or more and 10 μg/cm$^2$ or less. In the case that the Ni elution amount in the treatment is within the above-mentioned range, the Ni reaction coating can be removed without damaging the effect of suppressing microorganism-propagation or other functions based on the topmost surface functional layer.

That is, in the case that the Ni amount which elutes in the treatment is less than the above-mentioned range, the effect of removing the Ni reaction coating may be insufficient and the microorganism-propagation suppressing effect of the member may not be sufficiently ensured. On the other hand, in the case that the Ni elution amount is more than the above-mentioned range, Ni in anti-fungus layer portions corresponding to the bottoms of the through holes elutes so that the portions are largely hollowed out. For this reason, a problem about the adhesiveness of the anti-fungus layer is caused and further the eluting Ni ions may be adsorbed on the topmost surface functional layer. Thus, external appearance defects, such as color evenness, trend to be generated and the discoloration resistance and corrosion resistance based on the topmost surface functional layer trend to fall.

The Ni elution amount $M_1$ (μg/cm$^2$) in the treatment can be obtained by measuring the Ni concentrations in the treatment solution before and after the treatment by ICP emission spectral analysis (calibration curve method) and using the following equation (2):

$$M_{Ni} = (C_a \times V_a - C_b \times V_b)/Y \tag{2}$$

wherein $C_a$: Ni concentration (μg/mL) after the treatment, Cb: Ni concentration (μg/mL) before the treatment, $V_a$: treatment solution amount (mL) after the treatment, $V_b$: treatment solution amount (mL) before the treatment, and Y: surface area (cm$^2$) of the anti-fungus member.

In order to set the Ni elution amount within the above-mentioned range at the time of the electrolysis treatment or immersion treatment, it is advisable to adjust various conditions, for example, the concentration (pH) of the used treatment solution, the treatment temperature, the treatment time, the current density (in the case of the electrolysis treatment), and so on.

In the case that the Ni elution amount at the time of the electrolysis treatment or immersion treatment is outside the above-mentioned range, not only the anti-fungus layer components but also the topmost surface functional layer components may elute. When the topmost surface functional layer components elute in the above-mentioned treatment, the discoloration resistance or the corrosion resistance may become insufficient by a decrease in the thickness of this layer. The thickness of the topmost surface functional layer may be unevenly decreased over the whole. Thus, the dimensional precision of the member may fall. Furthermore, because of the elution of the topmost surface functional layer components, the member surface may not turn into a desired color, or this elution may cause the generation of color evenness.

Thus, at the time of the electrolysis treatment or immersion treatment, the concentration and the temperature of the treatment solution, the treatment time, and the current density in the electrolysis treatment are preferably set to conditions which do not cause the above-mentioned problems about the elution of the topmost surface functional layer components. The elution amount of the topmost surface functional layer components at the time of the above-mentioned treatment is preferably set to 1 mg/cm$^2$ or less, more preferably 0.1 mg/cm$^2$ or less, and most preferably 0 mg/cm$^2$. This elution amount of the topmost surface functional layer components can be usually attained by the treatment under conditions for setting the Ni elution amount within the above-mentioned range.

The elution amount of the topmost surface functional layer components at the time of the above-mentioned treatment can be obtained by analyzing the treatment solution before and after the treatment by. ICP emission spectral analysis (calibration curve method). From a change amount in the mass of the anti-fungus member before and after the above-mentioned treatment, the amount may also be obtained using the following equation (3):

$$M_2 = (W/Y) - M_1 \quad (3)$$

wherein $M_2$: elution amount (mg/cm$^2$) of the topmost surface functional layer components, and W: change amount in the mass of the anti-fungus member before and after the treatment.

The electrolysis treatment or immersion treatment may be applied to a member wherein the topmost surface functional layer is disposed by any method other than the above-mentioned wet plating treatment, chemical treatment and oxidization treatment. By adopting this treatment, the effect of suppressing microorganism-propagation is more surely secured.

EXAMPLES

The present invention will be described in detail hereinafter on the basis of examples. However, the following examples do not limit the present invention, and all modifications within the scope which does not depart from the above-mentioned and below-mentioned subject matters are included in the technical scope of the present invention.

Experiment 1

Stainless steel was used as bases to form samples under conditions as described below. First, a commercial available pre-plating treatment solution was used for the respective bases to perform degrease, etching, surface activation, and Ni strike plating successively. Thereafter, the following were used: the so-called Watts bath, which consisted of nickel sulfate: 240 g/L. nickel chloride: 45 g/L, and boric acid: 30g/L; and a bath wherein phosphoric acid and phosphorous acid were added to a bath wherein the respective components of the Watts bath were increased or decreased and cobalt sulfate, ferrous sulfate, a surfactant, a brightening agent and so on were appropriately added thereto. Electric current of 1 to 10 A/dm$^2$ was then sent thereto so that a plating having a thickness of about 5 μm was applied thereto. In this way, an anti-fungus layer was formed. About some of the bases, hydrogen-charging or baking was performed to increase the hydrogen content in the plating coating (in the anti-fungus layer).

Thereafter, a topmost surface functional layer was formed to produce each sample. The topmost surface functional layer made to a Cr plating was formed by: adding hydrofluorosilicic acid, sodium hydrofluorosilicate, strontium sulfate, sodium alkylsulfonate, hydrochloric acid, hydroiodic acid and so on appropriately to the so-called sergeant bath consisted of anhydrous chromic acid: 250 g/l and sulfuric acid: 2.5 g/L or a bath wherein the respective components of the sergeant bath were increased or decreased; using the resultant bath; sending electric current of 10 to 50 A/dm$^2$ thereto; and applying a plating having a thickness of about 5 μm to the base.

The topmost surface functional layer made to a chromium oxide coating was formed by: adding phosphoric acid, hydrochloric acid, ammonium fluoride and so on appropriately to a bath consisted of anhydrous chromic acid: 25 g/l, sulfuric acid: 3 g/L, and nitric acid: 4 g/L; using the resultant bath; and conducting chemical treatment (chromate treatment).

The topmost surface functional layer made to a zinc plating was formed by using a commercially available plating bath ("Asahi zincol", made by Kamimura Kogyo Co., Ltd.) and conducting plating treatment under conditions of 30° C. and 1 A/dm$^2$ for several seconds to 5 minutes.

In the sample wherein a zinc-rich paint was used in the topmost surface functional layer, the topmost surface functional layer was formed by spraying a commercially available zinc-rich paint ("Nipezinkey #1000", made by Nippon Paint Co., Ltd.) at a spray amount of 50 to 100 mL/min. and a spray distance of 30to 50 cm by means of an air sprayer for several seconds to 10 seconds.

The topmost surface functional layer made to an acryl resin was formed by performing electrodeposition coating, using a commercially available aqueous acryl resin ("Elecoat CM", made by Shimizu Co., Ltd.) having a solid content of 1 to 10% mass under an electrodeposition condition of 70 V for several seconds to 10 seconds and then drying the resultant coating for baking.

The topmost surface functional layer made to a TiN coating was formed by AIP with the introduction of N$_2$ gas, the application of an arc electric current of 100 to 175 A and a bias voltage of 50 to 75 V in a vacuum state having a pressure of about 1.33 Pa (1×10$^{-2}$ Torr).

Subsequently, the samples wherein the topmost surface functional layers were made to the Cr plating coating, the chromium oxide film, and zinc plating coating were subjected to anode electrolysis treatment in the respective plating baths or treatment baths at a constant electric current (1 A/dm$^2$) in such a manner that the time was adjusted to set the Ni elution amount to 1-2 µg/cm$^2$. They were then subjected to the following, evaluations. The samples wherein the zinc-rich paint, the acryl resin and the TiN coating were used for the topmost surface functional layers were subjected to the following evaluations without conducting the above-mentioned anode electrolysis treatment after the formation of the topmost surface functional layers.

(1) Area Ratio of Through Holes, and Thickness of the Topmost Surface Functional Layer Five fields of the topmost surface functional layer surface of each of the sample (fields: 10 µm×10 µm only about the chromate coating, and 100 µm×100 µm about the others) were observed with a scanning electron microscope. The area ratio S1 (%) of holes in the topmost surface functional layer surface was measured with an image processing device. A vertical section of the sample from the topmost surface of the surface treatment coating to the rear face of the base was observed with the scanning electron microscope. The ratio X (%) of the number of the through holes reaching the surface of the anti-fungus layer to the holes present in the topmost surface functional layer surface, the number of the holes being 20 or more, was calculated for each member.

From the above-mentioned area ratio S1 (%) and the ratio X (%) of the number of the through holes reaching the anti-fungus layer surface to the number of the holes present in the topmost surface functional layer surface, the area ratio S2 (%) of the through holes was calculated, using the following equation (1):

$$S2=S1 \times X/100 \qquad (1)$$

The thicknesses of the topmost surface functional layer obtained from the respective observed fields of the vertical section of the sample wherein the ratio X of the number of the through holes were obtained was averaged and the resultant value was used as the thickness of the topmost surface functional layer of the sample.

(2) Elution Amount of the Topmost Surface Functional Layer Components

About samples wherein the thickness of the topmost surface functional layer was made large (1 to 10 µm), measurement was made. Into a 500-mL beaker was put 50 mL of ion exchange water, and the temperature of the water was set to 30° C. The whole of the sample having a topmost surface functional layer area of 25 cm$^2$ was immersed in this water for one week, and then the amount of Ni in the ion exchange water was measured by ICP emission spectral analysis (calibration curve method). About the samples wherein the elution amount was unable to be obtained by ICP emission spectral analysis, a decrease in the mass thereof was measured to obtain the elution amount. The matter that the elution amount of the topmost surface functional layer components by ICP emission spectral analysis was substantially equal to the elution amount of the topmost surface functional layer components by the mass decrease was confirmed, using the samples wherein the elution amount can be measured by any one of these methods.

(3) Vickers Hardness

About samples wherein the thickness of the topmost surface functional layer was made large (1 to 10 µm), measurement was made. The hardness was measured from the topmost surface functional layer surface according to the rule of JIS Z 2244 in the state that power for the test was set to 0.25 N. However, the sample having a hardness Hv of less than 100 was evaluated as "<Hv 100", and the sample having a hardness Hv of more than 1000 was evaluated as ">Hv 1000".

(4) Natural Electrode Potential

Only when the topmost surface functional layer was made of the metal or alloy, the sample wherein the thickness of the topmost surface functional layer was made large (1 to 10 µm) was measured. The sample was immersed in water of 30° C. from which gas was removed, and a silver/silver chloride electrode was used as a reference electrode to measure the natural electrode potential. Thus, it was judged whether the metal or alloy was baser or nobler than Ni.

(5) Component Amount of the Anti-fungus Layer

Nitric acid was used to dissolve the anti-fungus layer therein. Thereafter, the Ni content and the P content were measured by ICP emission spectral analysis (calibration curve method).

About the hydrogen-adsorbing amount, the anti-fungus layer peeled mechanically from the base was continuously heated up to 350° C. at a temperature-raising speed of 12° C./min., and generated gas and the amount thereof were analyzed with an atmospheric pressure ionization mass spectrometer (API-MS). This coating analysis was according to a method disclosed in an already-reported document ("Kobe Seiko Technical Report" Vol.47, No.1, p24, April 1997) by Iwata et al.

(6) Ni Elution Amount

Into a 500-mL beaker was put 50 mL of ion exchange water, and the temperature of the water was raised to 30° C. The whole of the sample having a topmost surface functional layer area of 25 cm$^2$ was immersed into this water for one week, and subsequently the amount of Ni in the ion exchange water was obtained by ICP emission spectral analysis (calibration curve method).

(7) Anti-fungus Property Evaluation

Colon bacilli were used, and 0.5 ml of a solution wherein the concentration of each of various kinds of bacterial cells after cultivation was adjusted to $2 \times 10^5$ to $1 \times 10^6$ (CFU/mL) was dropped onto the sample. Thereafter, the upper face thereof was covered with a polyethylene film and they were adhered to each other. This was kept at 35° C. and a relative humidity of 90% or more under dark light for 2 hours, and subsequently the number of living bacteria (survival rate of the bacteria, %) was measured by a plate dilution method, and the resultant value was conversed to a value per sample. The case in which the survival rate was less than 5% was evaluated as ⊚, the case in which the rate was 5% or more and less than 20% was evaluated as ○, the case in which the rate was 20% or more and less than 50% was evaluated as Δ, and the case in which the rate was 50% or more was evaluated as x.

(8) Exhibition or Non-exhibition of the Effect of Denaturation of Proteins

An inactivation test of phages (a kind of virus the recipient of which is a bacterium) was made. In this test, a reduction in the number of the phages shows that proteins thereof are denatured so that the phages are inactivated and the infection ability thereof is lost. Therefore, the denaturation of the proteins can easily be examined. Thus, it is possible to examine effect on not only bacteria but also algae, mold, viruses and so on, the main component of which is a protein. Onto the sample was dropped 0.5 mL of a phage solution wherein the concentration thereof was beforehand adjusted to $2\times10^5$ to $1\times10^6$ (PFU/mL), and subsequently a piece of cover glass was adhered thereto.

This was kept at 30° C. for 4 hours, and subsequently the phages were washed out. Phage infection was attached by a double agar method, and then the phages were cultivated at 37° C. for 24 hours. The number of the produced plaques was counted to obtain the number of active phages and measure the survival rate thereof. The case in which the phage survival rate was less than 5% was evaluated as ⊚, the case in which the rate was 5% or more and less than 20% was evaluated as ○, the case in which the rate was 20% or more and less than 50% was evaluated as Δ, and the case in which the rate was 50% or more was evaluated as ×.

(9) Resistance Discoloration

According to JIS Z 2371, the sample was subjected to a saline water spray test for one day. The color difference before and after the test was measured with a color-difference meter. The case in which ΔE was less than 1 was evaluated as ⊚, the case in which ΔE was 1 or more and less than 3 was evaluated as ○, the case in which ΔE was 3 or more and less than 10 was evaluated as Δ, and the case in which ΔE was 10 or more was evaluated as ×.

The sample subjected to a sliding abrasion test [partner member: SUJ2 pin, load: 5000 kgf/m², 3 cm×100 reciprocations, dry manner] was also subjected to the same saline water spray test. The criteria or evaluation were the same as in the case that no sliding abrasion test was made.

Each of the samples produced by the above-mentioned method is shown in Tables 1 and 2, and the evaluation results are shown in Table 3. About total evaluation shown in Table 3, each of the samples was evaluated on the basis of the worst evaluation rank out of the 4 kinds of 4-rank evaluation results.

TABLE 1

| | | Topmost surface functional layer | | | | |
|---|---|---|---|---|---|---|
| Sample | Kind | Thickness (μm) | Through hole area ratio (%) | Elution amount (μg/cm²/week) | Natural electrode potential | Surface hardness |
| 1 | F | 0.005 | 0.5 | 0 | — | >1000 |
| 2 | A | 10 | 0.5 | 0.01 | Noble | 900 |
| 3 | F | 0.1 | 0 | 0 | — | >1000 |
| 4 | A | 0.2 | 13 | 0.01 | Noble | 900 |
| 5 | A | 0.1 | 0.5 | 0.01 | Noble | 900 |
| 6 | A | 0.1 | 0.5 | 0.01 | Noble | 900 |
| 7 | A | 0.1 | 0.5 | 0.01 | Noble | 900 |
| 8 | A | 0.1 | 0.5 | 0.01 | Noble | 900 |
| 9 | A | 0.1 | 0.5 | 0.01 | Noble | 900 |
| 10 | C | 0.01 | 10 | 2 | Base | 650 |
| 11 | E | 0.05 | 0.01 | 0 | — | <100 |
| 12 | D | 0.5 | 1 | 0.1 | — | <100 |
| 13 | E | 0.2 | 0.1 | 0 | — | <100 |
| 14 | A | 0.01 | 0.01 | 0.01 | Noble | 450 |
| 15 | A | 0.01 | 0.01 | 0.01 | Noble | 500 |
| 16 | A | 0.01 | 0.01 | 0.01 | Noble | 700 |
| 17 | A | 0.01 | 0.01 | 0.01 | Noble | 800 |
| 18 | F | 0.01 | 10 | 0 | — | >1000 |
| 19 | F | 5 | 0.001 | 0 | — | >1000 |
| 20 | B | 5 | 10 | 0 | — | >1000 |
| 21 | F | 5 | 0.5 | 0 | — | >1000 |
| 22 | A | 0.2 | 0.5 | 0.01 | Noble | 900 |
| 23 | B | 0.2 | 0.5 | 0 | — | >1000 |

In Table 1, the kind of the topmost surface functional layer is as follows.
A: Cr plating,
B: chromate (chromium oxide) coating,
C: zinc plating,
D: zinc-rich paint,
E: aminoacryl resin, and
F: TiN coating.

TABLE 2

| | Anti-fungus layer | | | |
|---|---|---|---|---|
| Sample | Ni content (% by mass) | P content (% by mass) | Hydrogen content (% by mass) | Ni elution amount (μg/cm²/week) |
| 1 | 92 | 3 | 0.05 | 15 |
| 2 | 92 | 3 | 0.05 | 0.01 |
| 3 | 92 | 3 | 0.05 | 0 |
| 4 | 92 | 3 | 0.05 | 50 |
| 5 | 73 | 3 | 0.05 | 0.05 |
| 6 | 99.95 | 0 | 0.05 | 35 |
| 7 | 86.95 | 13 | 0.05 | 0.1 |
| 8 | 92 | 3 | 0.00005 | 0.5 |
| 9 | 92 | 3 | 2 | 72 |
| 10 | 92 | 3 | 0.05 | 0.05 |
| 11 | 92 | 3 | 0.05 | 2.4 |
| 12 | 92 | 3 | 0.05 | 12 |
| 13 | 92 | 3 | 0.05 | 8.8 |
| 14 | 80 | 3 | 0.05 | 0.8 |
| 15 | 92 | 0.1 | 0.05 | 1.2 |
| 16 | 92 | 10 | 0.05 | 14 |
| 17 | 92 | 3 | 0.0001 | 14 |
| 18 | 92 | 3 | 0.9 | 45 |
| 19 | 92 | 1 | 0.05 | 0.1 |
| 20 | 92 | 3.5 | 0.05 | 25 |
| 21 | 92 | 3 | 0.001 | 25 |
| 22 | 92 | 3 | 0.1 | 11 |
| 23 | 92 | 3 | 0.05 | 4.8 |

TABLE 3

| Sample | Anti-fungus Property | Protein Denaturation | Discoloration resistance | Discoloration resistance After sliding abrasion | Total Evaluation |
|---|---|---|---|---|---|
| 1 | ◎ | ◎ | △ | x | x |
| 2 | x | x | ◎ | ◎ | x |
| 3 | x | x | ◎ | ◎ | x |
| 4 | △ | △ | x | x | x |
| 5 | x | x | ◎ | ◎ | x |
| 6 | x | x | ◎ | ◎ | x |
| 7 | x | x | ◎ | ◎ | x |
| 8 | x | x | ◎ | ◎ | x |
| 9 | ◎ | ◎ | x | x | x |
| 10 | △ | △ | △ | x | x |
| 11 | ◎ | ◎ | ◎ | △ | △ |
| 12 | ◎ | ◎ | ◎ | △ | △ |
| 13 | ◎ | ◎ | ○ | △ | △ |
| 14 | ○ | ○ | ◎ | △ | △ |
| 15 | ◎ | ○ | ◎ | ○ | ○ |
| 16 | ◎ | ◎ | ◎ | ○ | ○ |
| 17 | ◎ | ○ | ◎ | ◎ | ○ |
| 18 | ○ | ○ | ○ | ○ | ○ |
| 19 | ○ | ○ | ◎ | ◎ | ○ |
| 20 | ○ | ○ | ○ | ○ | ○ |
| 21 | ◎ | ◎ | ○ | ○ | ○ |
| 22 | ◎ | ◎ | ◎ | ◎ | ◎ |
| 23 | ◎ | ◎ | ◎ | ◎ | ◎ |

Samples Nos. 11 to 23 are examples which satisfy the requirements of both the first and second embodiments of the present invention, and have good anti-fungus property.

Samples Nos. 1 to 10 are comparative examples which neither satisfy the requirements of the first nor second embodiments of the present invention, and have the following inconveniences.

In samples Nos. 5 to 8 out of the samples (Nos. 5 to 9) wherein the Ni, P and hydrogen contents do not satisfy the requirements of the present invention, the anti-fungus property and the protein denaturation effect are insufficient. In sample No.9, wherein the hydrogen content is more than the range of the present invention, the anti-fungus property and the protein denaturation effect are sufficient but the discoloration resistance falls and the effect of the topmost surface functional layer is damaged.

In the samples (Nos. 1 to 4, and 10) wherein the through hole area ratio, the thickness and the component elution amount of the topmost surface functional layer do not satisfy the requirements of the present invention, the anti-fungus property, the protein denaturation effect and/or the discoloration resistance are insufficient.

Furthermore, in the case that the metal contained in the topmost surface functional layer is nobler than Ni, the anti-fungus property and the protein denaturation effect are superior to the case that the metal is baser. In the samples having a superior surface hardness, the discoloration resistance is also good after the sliding abrasion test.

Experiment 2

Plural samples wherein their topmost surface functional layer was a Cr plating coating and plural samples wherein their topmost surface functional layer was a chromium oxide coating were produced in the same was as in Experiment 1. These samples were subjected to immersion treatment or electrolysis treatment under the following conditions.

[Immersion Treatment]

As an immersion bath, there was used a bath wherein NaCl was dissolved in hydrochloric acid in such a manner that NaCl would have a concentration of 50 g/L and further the pH of the bath itself was adjusted with sodium hydroxide. The temperature of this immersion bath was set to 30° C., and the sample was immersed therein for 100 to 10000 seconds. The Ni concentrations in the immersion bath before and after the immersion treatment were measured by ICP emission spectral analysis (calibration curve method), and the Ni elution amount in the immersion treatment was obtained using the above-mentioned equation (2).

[Electrolysis Treatment]

The Cr plating bath used when the sample wherein its topmost surface functional layer was made to the Cr plating coating was produced was used to conduct constant-current anode electrolysis treatment under the following conditions: a temperature of 30° C., a current density of 0.1 to 15 A/dm$^2$, and a time of 10 to 1000 seconds. The Ni elution amount in this treatment was obtained by the same method as in the above-mentioned immersion treatment.

About the samples after the immersion treatment and the samples after the electrolysis treatment, the above-mentioned anti-fungus property evaluation (7) and discoloration resistance evaluation (9) were made. The results are shown in graphs of FIGS. 3 to 6.

Figure 3:
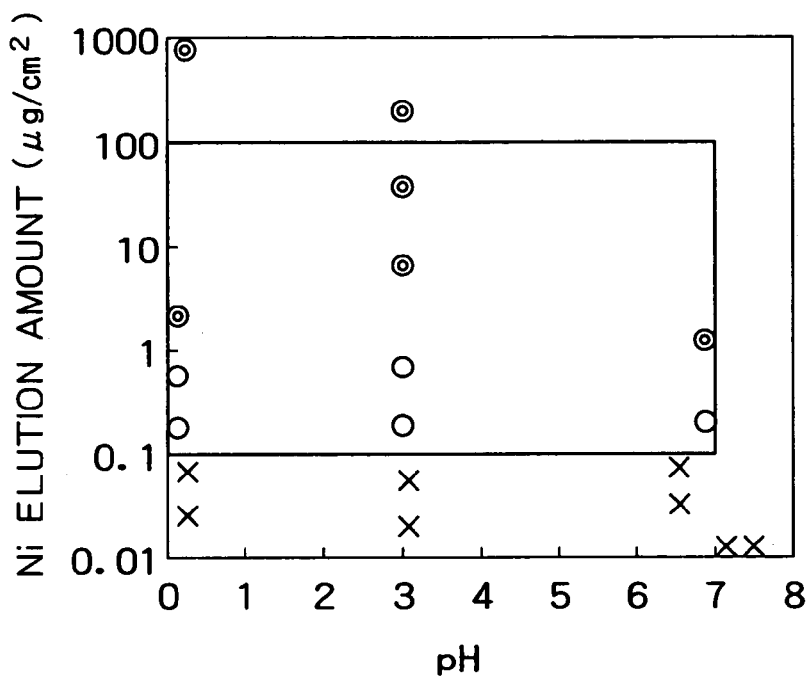
FIG. 3 is a graph showing relationship between immersion treatment conditions for samples of Example and the anti-fungus property thereof.
Figure 4:
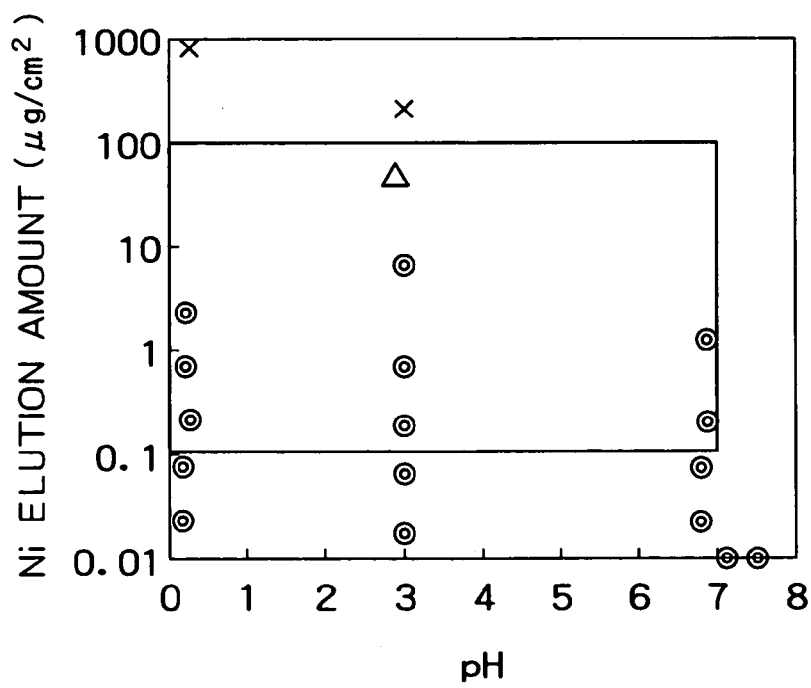
FIG. 4 is a graph showing relationship between immersion treatment conditions for samples of Example and the discoloration resistance thereof.

FIGS. 3 and 4 are graphs wherein the pH of the immersion treatment bath is taken as the transverse axis and the Ni elution amount at the time of the immersion treatment is taken as the vertical axis. About points in FIG. 3, the anti-fungus property evaluation results of the samples are marked in accordance with the criteria in the above-mentioned (7). About points in FIG. 4, the discoloration resistance evaluation results of the samples are marked in accordance with the criteria in the above-mentioned (9).

When FIG. 3 is viewed, it-is understood that in the case that the pH of the treatment bath is more than 7, the effect of removing the Ni reaction coating is insufficient since the Ni elution amount is small in the immersion treatment and the anti-fungus property of this sample is also poor. In the samples subjected to the treatment in which the Ni elution amount is less than 0.1 µg/cm$^2$ at the time of this treatment even if the pH of the treatment bath is more than 7, the anti-fungus property is poor and the removal of the Ni reaction coating is insufficient.

When FIG. 4 is viewed, in the samples subjected to the treatment wherein the Ni elution amount is more than 100 µg/cm$^2$ at the time of this treatment, the discoloration resistance is poor.

Figure 5:
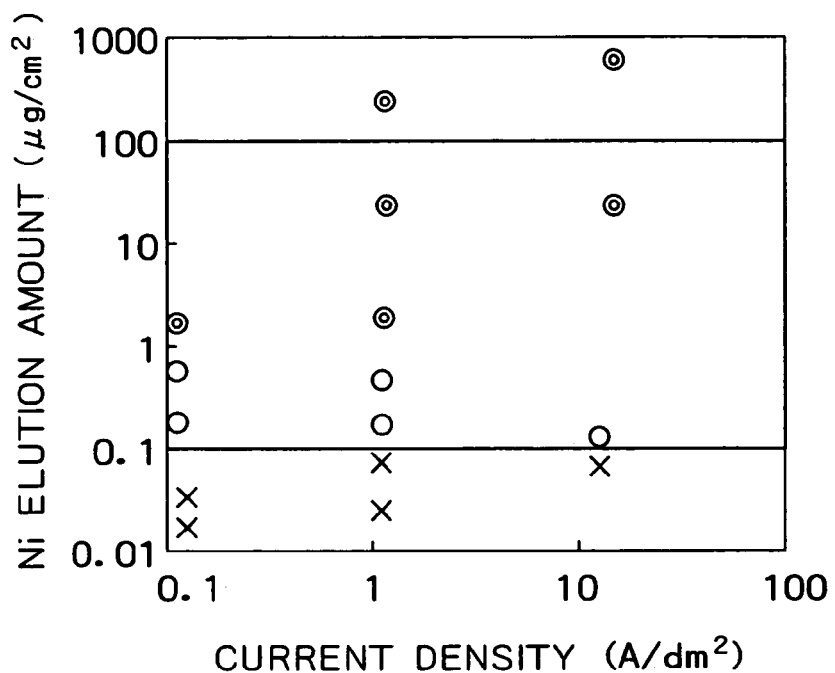
FIG. 5 is a graph showing relationship between electrolysis treatment conditions for samples of Example and the anti-fungus property thereof.
Figure 6:
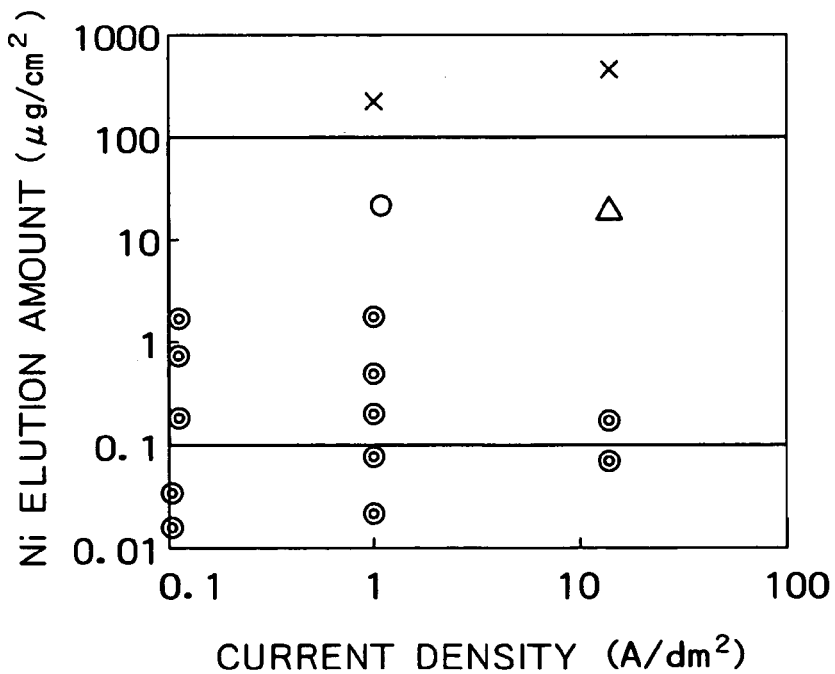
FIG. 6 is a graph showing relationship between electrolysis treatment conditions for samples of Example and the discoloration resistance thereof.

On the other hand, FIGS. 5 and 6 are graphs wherein the current density at the time of the electrolysis treatment is taken as the transverse axis and the Ni elution amount at the time of the electrolysis treatment is taken as the vertical axis. About points in FIG. 5, the anti-fungus property evaluation results of the samples are marked in accordance with the criteria in the above-mentioned (7). About points in FIG. 6, the discoloration resistance evaluation results of the samples are marked in accordance with the criteria in the above-mentioned (9).

When FIG. 5 is viewed, in the samples subjected to the treatment in which the Ni elution amount is less than 0.1 µg/cm$^2$ at the time of this treatment, the anti-fungus property is poor and the removal of the Ni reaction coating is insufficient.

When FIG. 6 is viewed, in the samples subjected to the treatment wherein the Ni elution amount is more than 100 µg/cm$^2$ at the time of this treatment, the discoloration resistance is poor.

INDUSTRIAL APPLICABILITY

As described above, the present invention can provide a member having unprecedented properties by disposing a surface treatment coating having the above-mentioned anti-fungus layer capable of giving the effect of suppressing microorganism-propagation and further having a topmost surface functional layer having a structure which gives other properties required for the member and does not hinder the effect of suppressing microorganism-propagation based on the anti-fungus layer.

For example, in the member of the present invention, the above-mentioned chromium-based compound is adopted as the material of the topmost surface functional layer, whereby the member becomes superior in anti-fungus property and discoloration resistance; therefore, the member is particularly suitable for water-associated articles used in food-manufacturing facilities, kitchen equipment, sanitary parts such as lavatories, washstands and water supply pipes, washing machines, drying machines, water channels for cooling water, ships, ship parts, underwater structures, ocean facilities and so on.

The invention claimed is:

1. A member coated with a surface treatment coating comprising a layer (2) having at least one of an anti-bacteria, anti-mold and anti-algae property present between a topmost surface functional layer (3) and a base (1),
   wherein the thickness of the layer (3) is from 0.01 µm to 5 µm,
   holes reaching the surface of the layer (2) are present in the layer (3) so as to penetrate the layer (3), the opening area ratio thereof to the total area when the layer (3) is viewed in plan being from 0.001 to 10%,
   the elution amount of components of the layer (3) is 1 µg/cm²/week or less when the member is immersed in still water at 30° C., and
   the layer (2) comprises, in mass %, 80% or more of Ni, 0.1 to 10% of P, and 0.0001 to 1% of hydrogen.

2. The member according to claim 1, wherein layer (3) contains a material made of Cr.

3. The member according to claim 1, wherein layer (3) has a surface hardness Hv (Vickers Pyramid Number) of 500 or more.

4. The member according to claim 1, wherein the layer (3) is a discoloration resistance functional layer made mainly of at least one selected from Cr, alloy containing 80% or more of Cr, Cr oxide, Cr carbide, Cr nitride, and complex oxide containing Cr.

5. A water-associated article comprising the member according to claim 4.

6. A process for producing the member according to claim 1, comprising forming an intermediate layer comprising layer (2) and layer (3) on base (1), and subsequently subjecting the resultant to electrolysis treatment or immersion treatment in an acidic solution having a pH of 7 or less in such a manner that the amount of Ni eluting into the acidic solution is from 0.1 to 100 µg/cm².

7. The production process according to claim 6, wherein the layer (3) is formed by wet plating treatment and subsequently the electrolysis treatment is conducted in the plating bath.

8. A member coated with a surface treatment coating comprising a layer (2) having at least one of an anti-bacteria, anti-mold and anti-algae property present between a topmost surface functional layer (3) and a base (1),
   wherein holes reaching the surface of the layer (2) are present in the layer (3) so as to penetrate the layer (3),
   the thickness of the layer (3) is from 0.01 µm to 5 µm,
   the elution amount of components of the layer (3) is 1 µg/cm²/week or less when the member is immersed in still water at 30° C.,
   the layer (2) comprises, in mass %, 80% or more of Ni, 0.1 to 10% of P, and 0.0001 to 1% of hydrogen, and
   the elution amount of Ni is from 0.1 to 50 µg/cm²/week when the member is immersed in still water at 30° C.

9. The member according to claim 8, wherein layer (3) contains a material made of Cr.

10. The member according to claim 8, wherein layer (3) has a surface hardness Hv of 500 or more.

11. The member according to claim 8, wherein the layer (3) is a discoloration resistance functional layer made mainly of at least one selected from Cr, alloy containing 80% or more of Cr, Cr oxide, Cr carbide, Cr nitride, and complex oxide containing Cr.

12. A water-associated article comprising the member according to claim 11.

13. A process for producing the member according to claim 8, comprising forming an intermediate layer comprising layer (2) and layer (3) on base (1), and subsequently subjecting the resultant to electrolysis treatment or immersion treatment in an acidic solution having a pH of 7 or less in such a manner that the amount of Ni eluting into the acidic solution is from 0.1 to 100 µg/cm².

14. The production process according to claim 13, wherein the layer (3) is formed by wet plating treatment and subsequently the electrolysis treatment is conducted in the plating bath.

* * * * *

UNITED STATES PATENT AND TRADEMARK OFFICE
CERTIFICATE OF CORRECTION

PATENT NO.        : 7,244,452 B2                                            Page 1 of 1
APPLICATION NO.   : 10/466547
DATED             : July 17, 2007
INVENTOR(S)       : Urushihara et al.

It is certified that error appears in the above-identified patent and that said Letters Patent is hereby corrected as shown below:

On the title page, Item (30), the Foreign Application Priority Data is incorrect. Item (30) should read:
-- Item (30)    Foreign Application Priority Data
        Aug. 21, 2001   (JP)...........................2001-250465
        Apr. 18, 2002   (JP)...........................2002-116678 --

On the title page, Item (73), the Assignee is incorrect. Item (73) should read:

-- Item (73) Assignee: Kabushiki Kaisha Kobe Seiko Sho (Kobe Steel, Ltd.),
        Kobe-shi (JP)--

Signed and Sealed this

Fourth Day of September, 2007

JON W. DUDAS
*Director of the United States Patent and Trademark Office*